(12) United States Patent
Liu et al.

(10) Patent No.: US 9,020,734 B2
(45) Date of Patent: *Apr. 28, 2015

(54) METHOD, APPARATUS, SIGNALS AND MEDIA, FOR SELECTING OPERATING CONDITIONS OF A GENSET

(71) Applicant: Conversant Intellectual Property Management Inc., Ottawa (CA)

(72) Inventors: Wei Liu, Mississauga (CA); Nicolas Louis Bouchon, Vancouver (CA)

(73) Assignee: GE Hybrid Technologies, LLC, Albany, NY (US)

(*) Notice: Subject to any disclaimer, the term of this patent is extended or adjusted under 35 U.S.C. 154(b) by 0 days.

This patent is subject to a terminal disclaimer.

(21) Appl. No.: 14/148,436

(22) Filed: Jan. 6, 2014

(65) Prior Publication Data

US 2014/0121879 A1 May 1, 2014

Related U.S. Application Data

(63) Continuation of application No. 13/674,624, filed on Nov. 12, 2012, now Pat. No. 8,655,570, which is a continuation of application No. 11/821,855, filed on Jun. 26, 2007, now Pat. No. 8,346,416.

(60) Provisional application No. 60/816,503, filed on Jun. 26, 2006.

(51) Int. Cl.
*G06F 19/00* (2011.01)
*G06G 7/70* (2006.01)
(Continued)

(52) U.S. Cl.
CPC .............. *B60W 20/1082* (2013.01); *B60K 6/48* (2013.01); *B60L 11/126* (2013.01); *B60W 10/06* (2013.01);
(Continued)

(58) Field of Classification Search
USPC ....... 701/22, 99; 290/40 R, 40 A, 40 B, 40 C; 903/902, 903, 905, 906; 180/65.1, 180/65.21, 65.28, 65.285; 700/287
See application file for complete search history.

(56) References Cited

U.S. PATENT DOCUMENTS 2,916,635 A 12/1959 Nicita
3,225,542 A 12/1965 Hansen et al.
(Continued)

FOREIGN PATENT DOCUMENTS

CA 2351911 A1 12/2001
EP 0867323 A2 9/1998
(Continued)

OTHER PUBLICATIONS

Zhang, Rongjun, et al.; "Control of Hybrid Dynamical Systems for Electric Vehicles"; Proceedings of the American Control Conference; Jun. 25-27, 2001; 6 pages.
(Continued)

*Primary Examiner* — Khoi Tran
*Assistant Examiner* — Jaime Figueroa
(74) *Attorney, Agent, or Firm* — Conley Rose, P.C.; J. Robert Brown, Jr.

(57) ABSTRACT

An apparatus for selecting operating conditions of a genset, the apparatus including a processor circuit configured to select a set of operating points from a plurality of operating points of the genset each comprising an engine speed in a generator electrical output value and a plurality of cost values associated with operating the genset at respective operating points such that the sum of the cost values associated with the operating points in said set is minimized and such that the engine speed increases or decreases monotonically with monotonically increasing or decreasing electrical power output values.

24 Claims, 9 Drawing Sheets

(51) Int. Cl.
*B60W 20/00* (2006.01)
*B60K 6/48* (2007.10)
*B60L 11/12* (2006.01)
*B60W 10/06* (2006.01)
*F01N 11/00* (2006.01)
*H02P 9/04* (2006.01)
*G01F 13/00* (2006.01)
*G01N 19/00* (2006.01)
*G06F 15/00* (2006.01)
*B60W 10/08* (2006.01)

(52) U.S. Cl.
CPC ............ *B60W 20/00* (2013.01); *B60W 2530/14* (2013.01); *F01N 11/00* (2013.01); *Y02T 10/56* (2013.01); *Y02T 10/6217* (2013.01); *Y02T 10/6221* (2013.01); *Y02T 10/7005* (2013.01); *Y02T 10/7077* (2013.01); *Y02T 10/47* (2013.01); *B60W 20/10* (2013.01); *H02P 9/04* (2013.01); *Y10S 903/902* (2013.01); *G01F 13/00* (2013.01); *G01N 19/00* (2013.01); *G06F 15/00* (2013.01); *B60W 10/08* (2013.01); *Y10S 903/903* (2013.01); *Y10S 903/905* (2013.01); *Y10S 903/906* (2013.01)

(56) References Cited

U.S. PATENT DOCUMENTS

| | | | |
|---|---|---|---|
| 3,261,007 | A | 7/1966 | Frisch |
| 4,083,052 | A | 4/1978 | Metcalf |
| 4,407,132 | A | 10/1983 | Kawakatsu et al. |
| 4,475,105 | A | 10/1984 | Kurosawa |
| 4,905,544 | A | 3/1990 | Ganoung |
| 5,327,992 | A | 7/1994 | Boll |
| 5,343,970 | A | 9/1994 | Severinsky |
| 5,345,761 | A | 9/1994 | King et al. |
| 5,547,433 | A | 8/1996 | Yang |
| 5,898,282 | A | 4/1999 | Drozdz et al. |
| 5,939,794 | A | 8/1999 | Sakai et al. |
| 6,009,965 | A | 1/2000 | Takanohashi et al. |
| 6,054,844 | A * | 4/2000 | Frank .............................. 322/16 |
| 6,083,138 | A | 7/2000 | Aoyama et al. |
| 6,098,734 | A | 8/2000 | Kawamura |
| 6,242,873 | B1 | 6/2001 | Drozdz et al. |
| 6,266,956 | B1 | 7/2001 | Suzuki et al. |
| 6,314,346 | B1 | 11/2001 | Kitajima et al. |
| 6,319,168 | B1 | 11/2001 | Morris et al. |
| 6,335,610 | B1 | 1/2002 | Winstead |
| 6,421,599 | B1 | 7/2002 | Lippa et al. |
| 6,480,767 | B2 | 11/2002 | Yamaguchi et al. |
| 6,500,089 | B2 | 12/2002 | Lasson et al. |
| 6,519,513 | B2 | 2/2003 | Nakagawa et al. |
| 6,555,991 | B1 | 4/2003 | Zettel et al. |
| 6,574,535 | B1 | 6/2003 | Morris et al. |
| 6,662,096 | B2 | 12/2003 | Komiyama et al. |
| 6,715,572 | B2 | 4/2004 | Shimabukuro et al. |
| 6,741,923 | B2 | 5/2004 | Katakura et al. |
| 6,768,621 | B2 | 7/2004 | Arnet et al. |
| 6,809,429 | B1 | 10/2004 | Frank |
| 6,879,054 | B2 | 4/2005 | Gosselin |
| 6,909,200 | B2 | 6/2005 | Bouchon |
| 6,991,052 | B2 | 1/2006 | Nogi et al. |
| 7,017,348 | B2 | 3/2006 | Tajima et al. |
| 7,024,290 | B2 | 4/2006 | Zhao et al. |
| 7,178,618 | B2 | 2/2007 | Komeda et al. |
| 7,223,203 | B2 | 5/2007 | Yamazaki et al. |
| 7,315,774 | B2 | 1/2008 | Morris |
| 7,455,133 | B2 * | 11/2008 | Kaneko et al. ........... 180/65.285 |
| 7,480,555 | B2 | 1/2009 | Jacobs |
| 7,549,292 | B2 | 6/2009 | Peck et al. |
| 7,563,730 | B2 | 7/2009 | Forbes et al. |
| 7,577,507 | B2 | 8/2009 | Morris |
| 7,728,448 | B2 | 6/2010 | Bouchon et al. |
| 8,346,416 | B2 | 1/2013 | Liu et al. |
| 8,655,570 | B2 | 2/2014 | Liu et al. |
| 2001/0039230 | A1 | 11/2001 | Severinksy et al. |
| 2002/0065165 | A1 | 5/2002 | Lasson et al. |
| 2002/0113441 | A1 | 8/2002 | Obayashi |
| 2003/0173126 | A1 * | 9/2003 | Gosselin ....................... 180/65.3 |
| 2004/0015255 | A1 | 1/2004 | Davis |
| 2004/0020206 | A1 | 2/2004 | Sullivan et al. |
| 2004/0074682 | A1 | 4/2004 | Fussey et al. |
| 2004/0163860 | A1 * | 8/2004 | Matsuzaki et al. ........... 180/65.2 |
| 2004/0164616 | A1 | 8/2004 | Obayashi et al. |
| 2004/0174125 | A1 | 9/2004 | Wilton et al. |
| 2004/0245947 | A1 * | 12/2004 | Wilton et al. .................. 318/139 |
| 2004/0254695 | A1 | 12/2004 | Komiyama et al. |
| 2004/0255904 | A1 | 12/2004 | Izawa et al. |
| 2005/0024061 | A1 | 2/2005 | Cox et al. |
| 2005/0057098 | A1 | 3/2005 | Bouchon |
| 2005/0080537 | A1 | 4/2005 | Cawthorne et al. |
| 2005/0246076 | A1 | 11/2005 | Chen et al. |
| 2006/0106524 | A1 * | 5/2006 | Schmitz et al. ............... 701/112 |
| 2006/0108163 | A1 | 5/2006 | Kitano et al. |
| 2006/0122737 | A1 | 6/2006 | Tani et al. |
| 2006/0237247 | A1 * | 10/2006 | Severinsky et al. .......... 180/65.4 |
| 2006/0276288 | A1 * | 12/2006 | Iwanaka et al. .................... 475/5 |
| 2007/0074516 | A1 | 4/2007 | Peck et al. |
| 2007/0149348 | A1 | 6/2007 | Holmes et al. |
| 2007/0262586 | A1 | 11/2007 | Bouchon et al. |
| 2008/0059013 | A1 | 3/2008 | Liu et al. |
| 2008/0236913 | A1 | 10/2008 | Ichimoto |

FOREIGN PATENT DOCUMENTS

| | | |
|---|---|---|
| EP | 1375237 A2 | 1/2004 |
| GB | 2267364 A | 12/1993 |
| JP | 01144101 A | 6/1989 |
| WO | 0242110 A1 | 5/2002 |
| WO | 02058209 A1 | 7/2002 |
| WO | 2004071800 A1 | 8/2004 |

OTHER PUBLICATIONS

Lin, Chan-Chiao, et al.; "Control System Development for an Advanced-Technology Medium-Duty Hybrid Electric Truck"; International Truck & Bus Meetings & Exhibition; Nov. 2003; 10 pages.
Chen, Jyh-Shin, et al.; "Learning Energy Management Strategy for Hybrid Electric Vehicles"; IEEE; 2005; 6 pages.
Lin, Chan-Chiao, et al.; "A Stochastic Control Strategy for Hybrid Electric Vehicles"; Proceeding of the 2004 American Control Conference; Jun. 30-Jul. 2, 2004; 6 pages.
Chan, C. C.; "The State of the Art of Electric and Hybrid Vehicles"; Proceedings of the IEEE; vol. 90; No. 2; Feb. 2002; 29 pages.
Musardo, Cristian, et al.; "A-ECMS: An Adaptive Algorithm for Hybrid Electric Vehicle Energy Management"; Proceedings of the 44th IEEE Conference on Decision and Control; Seville, Spain; Dec. 12-15, 2005; 8 pages.
Arnolds, M.B.; "Series Hybrid Powertrain Optimization and Control"; DCT Report No. 2005-26; TU/e Master Thesis Report; Mar. 2005; 82 pages.
Rahman, Z., et al.; "A Study of Design Issues on Electrically Peaking Hybrid Electric Vehicle for Diverse Urban Driving Patterns"; Society of Automotive Engineers, Inc.; 1999; 9 pages.
Won, Jong-Seob, et al.; "Intelligent Energy Management Agent for a Parallel Hybrid Vehicle"; Proceedings of the American Control Conference; IEEE; Denver, Colorado; Jun. 4-6, 2003; 6 pages.
Johnson, Valerie H., et al.; "HEV Control for Real-Time Optimization of Fuel Economy and Emissions"; Society of Automotive Engineers, Inc.; 2000; 15 pages.
Liu, Wei, et al.; U.S. Appl. No. 11/821,855, filed Jun. 26, 2007; Title: Method, Apparatus, Signals and Media, for Selecting Operating Conditions of a Genset.
Liu, Wei, et al.; U.S. Appl. No. 13/674,624, filed Nov. 12, 2012; Title: Method, Apparatus, Signals and Media, for Selecting Operating Conditions of a Genset.
Liu, Wei, et al.; U.S. Appl. No. 13/674,552, filed Nov. 12, 2012; Title: Method, Apparatus, Signals and Media, for Selecting Operating Conditions of a Genset.

(56) References Cited

OTHER PUBLICATIONS

Office Action dated Jan. 3, 2011; U.S. Appl. No. 11/821,855, filed Jun. 26, 2007; 7 pages.
Office Action dated Apr. 12, 2011; U.S. Appl. No. 11/821,855, filed Jun. 26, 2007; 26 pages.
Final Office Action dated Oct. 13, 2011; U.S. Appl. No. 11/821,855, filed Jun. 26, 2007; 18 pages.
Notice of Allowance dated Aug. 13, 2012; U.S. Appl. No. 11/821,855, filed Jun. 26, 2007; 7 pages.
Office Action dated Mar. 7, 2013; U.S. Appl. No. 13/674,624, filed Nov. 12, 2012; 14 pages.
Notice of Allowance dated Oct. 7, 2013; U.S. Appl. No. 13/674,624, filed Nov. 12, 2012; 12 pages.
Office Action dated Mar. 15, 2013; U.S. Appl. No. 13/674,552, filed Nov. 12, 2012; 17 pages.
PCT International Search Report; Application No. PCT/CA2007/001135; Oct. 10, 2007; 2 pages.
PCT Written Opinion of the International Searching Authority; Application No. PCT/CA2007/001135; Oct. 10, 2007; 5 pages.
European Supplementary Search Report; Application No. 07720049; Mar. 16, 2011; 4 pages.
European Supplementary Search Report; Application No. 07800541; Nov. 4, 2009; 5 pages.
European Supplementary Search Report; Application No. 07719724; Jan. 25, 2011; 5 pages.

* cited by examiner

| Power [kW] | Operating Conditions | Speed [rpm] | | | | | | | | | |
|---|---|---|---|---|---|---|---|---|---|---|---|
| | | 3400 | 3200 | 3000 | 2800 | 2600 | 2400 | 2200 | 2000 | 1800 | 1600 |
| No Load | Fuel | | | | | | | | 0.040 | 0.040 | 0.000 |
| | HC | | | | | | | | 0.334 | 0.460 | 0.392 |
| | CO | | | | | | | | 0.796 | 1.000 | 0.818 |
| | NO$_x$ | | | | | | | | 0.014 | 0.000 | 0.010 |
| 5 kW | Fuel | | | | | | 0.119 | 0.119 | 0.119 | 0.079 | 0.079 |
| | HC | | | | | | 0.696 | 0.505 | 0.453 | 0.668 | 1.000 |
| | CO | | | | | | 0.247 | 0.183 | 0.183 | 0.243 | 0.337 |
| | NO$_x$ | | | | | | 0.063 | 0.066 | 0.064 | 0.048 | 0.048 |
| 10 kW | Fuel | 0.465 | 0.426 | 0.386 | 0.307 | 0.307 | 0.267 | 0.267 | 0.228 | 0.188 | 0.188 |
| | HC | 0.028 | 0.024 | 0.024 | 0.025 | 0.025 | 0.024 | 0.001 | 0.001 | 0.001 | 0.000 |
| | CO | 0.027 | 0.028 | 0.027 | 0.014 | 0.012 | 0.006 | 0.002 | 0.001 | 0.001 | 0.000 |
| | NO$_x$ | 0.271 | 0.253 | 0.243 | 0.155 | 0.149 | 0.137 | 0.119 | 0.103 | 0.119 | 0.129 |
| 15 kW | Fuel | 0.574 | 0.505 | 0.465 | 0.426 | 0.386 | 0.347 | 0.347 | 0.307 | 0.267 | 0.267 |
| | HC | 0.028 | 0.028 | 0.028 | 0.028 | 0.024 | 0.021 | 0.021 | 0.019 | 0.017 | 0.017 |
| | CO | 0.023 | 0.021 | 0.021 | 0.014 | 0.007 | 0.005 | 0.003 | 0.002 | 0.001 | 0.001 |
| | NO$_x$ | 0.338 | 0.328 | 0.322 | 0.188 | 0.176 | 0.174 | 0.180 | 0.251 | 0.241 | 0.251 |
| 20 kW | Fuel | 0.673 | 0.614 | 0.574 | 0.545 | 0.485 | 0.465 | 0.465 | 0.426 | 0.426 | |
| | HC | 0.028 | 0.028 | 0.025 | 0.024 | 0.021 | 0.021 | 0.021 | 0.017 | 0.017 | |
| | CO | 0.018 | 0.017 | 0.016 | 0.012 | 0.007 | 0.005 | 0.004 | 0.002 | 0.002 | |
| | NO$_x$ | 0.559 | 0.534 | 0.504 | 0.291 | 0.291 | 0.275 | 0.251 | 0.322 | 0.382 | |
| 25 kW | Fuel | 0.772 | 0.733 | 0.693 | 0.653 | 0.594 | 0.574 | 0.594 | 0.574 | 0.545 | |
| | HC | 0.024 | 0.024 | 0.021 | 0.021 | 0.021 | 0.017 | 0.014 | 0.017 | 0.017 | |
| | CO | 0.020 | 0.016 | 0.014 | 0.010 | 0.007 | 0.005 | 0.004 | 0.005 | 0.006 | |
| | NO$_x$ | 0.716 | 0.676 | 0.676 | 0.433 | 0.484 | 0.433 | 0.352 | 0.392 | 0.524 | |
| 30 kW | Fuel | 0.891 | 0.861 | 0.822 | 0.772 | 0.733 | 0.733 | 0.693 | | | |
| | HC | 0.021 | 0.017 | 0.017 | 0.021 | 0.014 | 0.014 | 0.017 | | | |
| | CO | 0.019 | 0.018 | 0.016 | 0.010 | 0.009 | 0.008 | 0.008 | | | |
| | NO$_x$ | 0.818 | 0.818 | 0.615 | 0.362 | 0.372 | 0.291 | 0.342 | | | |
| 35 kW | Fuel | 1.000 | 0.980 | 0.950 | 0.911 | 0.891 | | | | | |
| | HC | 0.017 | 0.014 | 0.014 | 0.014 | 0.014 | | | | | |
| | CO | 0.025 | 0.021 | 0.020 | 0.012 | 0.012 | | | | | |
| | NO$_x$ | 1.000 | 0.980 | 0.980 | 0.494 | 0.534 | | | | | |

FIG. 6

METHOD, APPARATUS, SIGNALS AND MEDIA, FOR SELECTING OPERATING CONDITIONS OF A GENSET

RELATED APPLICATIONS

This application is a continuation of U.S. patent application Ser. No. 13/674,624, filed Nov. 12, 2012, which is a continuation application of U.S. patent application Ser. No. 11/821,855, filed Jun. 26, 2007, now U.S. Pat. No. 8,346,416, issued on Jan. 1, 2013, which claims benefit of and priority to U.S. Provisional Application No. 60/816,503, filed Jun. 26, 2006, all of which are incorporated herein by this reference in their entirety.

FIELD OF INVENTION

This invention relates generally to selecting operating conditions of an engine coupled to an electrical power generator for generating electrical power.

Advances in engine and hybrid vehicle technology have continually reduced harmful pollutant emissions. Hybrid vehicles having an engine driving a generator (a genset) cause emissions such as nitrogen oxides, carbon monoxide, hydrocarbons, and particulate matter. Each emission has a characteristic dependence on a power output level of the generator, and a rotational speed of the engine. Furthermore, given the present climate of higher prices of fossil fuels, there is a corresponding desire to reduce fuel consumption of the engine, thereby reducing the cost of operating the genset.

In particular, in electric hybrid vehicles, where the genset may supply electrical power to a drive motor and/or a charger for charging a storage battery, choosing operating points for the vehicle that minimize fuel consumption while simultaneously minimizing emissions or other operating conditions is a multi-variable problem and selecting operating points for the genset usually involves trading off between various emissions and fuel consumption to meet a desired criterion.

There remains a need for better methods and apparatus for selecting operating points of a genset, for use in hybrid vehicles and other applications.

SUMMARY OF THE INVENTION

In accordance with one aspect of the invention there is provided a method for selecting optimal operating conditions of a genset, the genset including an engine coupled to an electrical power generator, the genset having a plurality of operating points each including an engine speed value and a generator electrical power output value, and having a plurality of cost values associated with operating the genset at respective operating points. The method involves selecting a set of operating points from the plurality of operating points such that a sum of cost values associated with operating points in the set is minimized and such that the engine speed and generator electrical power output values of the operating points in the set increase or decrease monotonically.

The method may involve assigning a weight to each of the power output values such that cost values corresponding to more frequently demanded power output values are assigned a greater weight in the sum of cost values than cost values corresponding to less frequently demanded electrical power output values.

Assigning the weight may involve assigning greater weight to electrical power output values proximate a midpoint of a range of power outputs that the generator is capable of supplying.

The method may involve generating a record of received demands for power outputs during operation of the genset over a period of time, and assigning the weights may involve assigning greater weight to more frequently used power output values.

Generating the record may involve generating the record and updating the weights while operating the genset, and selecting may involve selecting a new set of operating points when the weights have been updated.

Selecting may involve successively applying a dynamic programming algorithm to select sets of operating points at successive power output values within a range of power outputs the generator is capable of supplying, and selecting a set of operating points corresponding to a last power output value in the range as the minimized set of operating points for the genset.

Applying the dynamic programming algorithm may involve producing a first plurality of the sums of cost values at a first power output value and memorizing a result of at least one of the first plurality of the sums. The method may further involve using at least some of the memorized results for producing a further sum of cost values at a subsequent power output value.

Selecting may involve locating a minimum cost value at each power output value and successively applying the dynamic programming algorithm may involve first producing the sums of cost values corresponding to the minimum cost value at each successive power output value.

Locating the minimum cost value may involve locating an operating point corresponding to the minimum cost value using a golden section search technique.

The method may involve receiving a demand to supply power at a demanded power output value and operating the genset at an operating point in the set of operating points corresponding to the demanded power output value.

The genset may be used to generate electrical energy for use in a hybrid electrical vehicle and receiving the demand may involve receiving a demand to supply power to at least one of a drive motor, a charger operable to charge a storage element, and an accessory associated with the hybrid vehicle.

Receiving the demand to supply power to the charger may involve receiving a demand to supply power to the charger while the hybrid electric vehicle remains stationary.

Receiving the demand to supply power to the drive motor may involve receiving a drive signal from an operator foot pedal representing a desired drive power to be supplied by the drive motor to wheels of the hybrid vehicle.

The storage element may be operable to supply at least a first portion of the desired drive power, and receiving the demand may involve receiving a demand for a second portion of the desired drive power.

Receiving the demand to supply power to the charger may involve receiving a charge signal from a storage element controller, the charge signal being produced in response to a state of charge associated with the storage element.

The method may involve receiving a plurality of cost values.

The method may involve selecting a new set of operating points in response to receiving the plurality of cost values.

Selecting may involve selecting the set of genset operating points prior to operating the genset.

In accordance with another aspect of the invention there is provided an apparatus for selecting operating conditions of a genset, the genset including an engine coupled to an electrical power generator, the genset having a plurality of operating points each including an engine speed value and a generator electrical power output value, and having a plurality of cost values associated with operating the genset at respective operating points. The apparatus includes provisions for selecting a set of operating points from the plurality of operating points such that a sum of cost values associated with operating points in the set is minimized and such that the engine speed and generator electrical power output values of the operating points in the set increase or decrease monotonically.

The apparatus may include provisions for assigning a weight to each of the power output values such that cost values corresponding to more frequently demanded power output values are assigned a greater weight in the sum of cost values than cost values corresponding to less frequently demanded electrical power output values.

The provisions for assigning the weight may include provisions for assigning greater weight to electrical power output values proximate a midpoint of a range of power output values that the generator is capable of supplying.

The apparatus may include provisions for generating a record of received demands for power outputs during operation of the genset over a period of time, and the provisions for assigning the weights may include provisions for assigning greater weight to more frequently used power output values.

The provisions for generating the record may include provisions for updating the weights while operating the genset, and the provisions for selecting may be operably configured to select a new set of operating points when the weights have been updated.

The provisions for selecting may include provisions for successively applying a dynamic programming algorithm to select sets of operating points at successive power output values within a range of power outputs the generator is capable of supplying and provisions for selecting a set of operating points corresponding to a last power output value in the range as the minimized set of operating points for the genset.

The provisions for applying the dynamic programming algorithm may include provisions for producing a first plurality of the sums of cost values at a first power output value, provisions for memorizing a result of at least one of the first plurality of the sums, and provisions for using at least some of the memorized results for producing a further sum of cost values at a subsequent power output value.

The provisions for selecting may include provisions for locating a minimum cost value at each power output value and the provisions for successively applying the dynamic programming algorithm may include provisions for first producing the sums of cost values corresponding to the minimum cost value at each successive power output value.

The provisions for locating the minimum cost value may include provisions for performing a golden section search technique.

The apparatus may include provisions for receiving a demand to supply power at a demanded power output value and provisions for operating the genset at an operating point in the set of operating points corresponding to the demanded power output value.

The genset may be used to generate electrical energy for use in a hybrid electrical vehicle and the provisions for receiving the demand may include provisions for receiving a demand to supply power to at least one of a drive motor, a charger operable to charge a storage element, and an accessory associated with the hybrid vehicle.

The provisions for receiving the demand to supply power to the charger may include means for receiving a demand to supply power to the charger while the hybrid electric vehicle remains stationary.

The storage element may include at least one of a storage battery, a capacitor, and an electrically coupled flywheel.

The provisions for receiving the demand to supply power to the drive motor may include provisions for receiving a drive signal from an operator foot pedal representing a desired drive power to be supplied by the drive motor to wheels of the hybrid vehicle.

The storage element may be operable to supply at least a first portion of the desired drive power, and the demand may include a demand for a second portion of the desired drive power.

The provisions for receiving the demand to supply power to the charger may include provisions for receiving a charge signal from a storage element controller, the charge signal being produced in response to a state of charge associated with the storage element.

The apparatus may include provisions for receiving a plurality of cost values.

The apparatus may include provisions for selecting a new set of operating points in response to receiving the plurality of cost values.

The provisions for selecting may include provisions for selecting the set of genset operating points prior to operating the genset.

In accordance with another aspect of the invention there is provided an apparatus for selecting operating conditions of a genset, the genset including an engine coupled to an electrical power generator, the genset having a plurality of operating points each including an engine speed value and a generator electrical power output value, and having a plurality of cost values associated with operating the genset at respective operating points. The apparatus includes a processor circuit operable to select a set of operating points from the plurality of operating points such that a sum of cost values associated with operating points in the set is minimized and such that the engine speed and generator electrical power output values of the operating points in the set increase or decrease monotonically.

The processor circuit may be operably configured to assign a weight to each of the power output values such that cost values corresponding to more frequently demanded power output values are assigned a greater weight in the sum of cost values than cost values corresponding to less frequently demanded electrical power output values.

The processor circuit may be operably configured to assign greater weight to electrical power output values proximate a midpoint of a range of power outputs that the generator is capable of supplying.

The processor circuit may be operably configured to generate a record of received demands for power outputs during operation of the genset over a period of time, and to assign greater weight to more frequently used power output values.

The processor circuit may be operably configured to update the weights while operating the genset and to select a new set of operating points when the weights have been updated.

The processor circuit may be operably configured to successively apply a dynamic programming algorithm to select sets of operating points at successive power output values within a range of power outputs the generator is capable of supplying and select a set of operating points corresponding to a last power output value in the range as the minimized set of operating points for the genset.

The processor circuit may be operably configured to produce a first plurality of the sums of cost values at a first power output value, memorize a result of at least one of the first plurality of the sums, and use at least some of the memorized results for producing a further sum of cost values at a subsequent power output value.

The processor circuit may be operably configured to locate a minimum cost value at each power output value and to apply the dynamic programming algorithm to first produce the sums of cost values corresponding to the minimum cost value at each successive power output value.

The processor circuit may be operably configured to locate the minimum cost value using a golden section search technique.

The processor circuit may be operably configured to receive a demand to supply power at a demanded power output value and to operate the genset at an operating point in the set of operating points corresponding to the demanded power output value.

The genset may be used to generate electrical energy for use in a hybrid electrical vehicle and the processor circuit may be operably configured to receive a demand to supply power to at least one of a drive motor, a charger operable to charge a storage element, and an accessory associated with the hybrid vehicle.

The processor circuit may be operably configured to receive the demand to supply power to the charger while the hybrid electric vehicle remains stationary.

The storage element may include at least one of a storage battery, a capacitor, and an electrically coupled flywheel.

The processor circuit may be operably configured to receive a drive signal from an operator foot pedal representing a desired drive power to be supplied by the drive motor to wheels of the hybrid vehicle.

The storage element may be operable to supply at least a first portion of the desired drive power, and the demand may include a demand for a second portion of the desired drive power.

The processor circuit may be operably configured to receive a charge signal from a storage element controller, the charge signal being produced in response to a state of charge associated with the storage element.

The processor circuit may be operably configured to receive a plurality of cost values.

The processor circuit may be operably configured to select a new set of operating points in response to receiving the plurality of cost values.

The processor circuit may be operably configured to select the set of genset operating points prior to operating the genset.

In accordance with another aspect of the invention there is provided a computer readable medium encoded with codes for directing a processor circuit to perform a method for selecting optimal operating conditions of a genset, the genset including an engine coupled to an electrical power generator, the genset having a plurality of operating points each including an engine speed value and a generator electrical power output value, and having a plurality of cost values associated with operating the genset at respective operating points. The method involves selecting a set of operating points from the plurality of operating points such that a sum of cost values associated with operating points in the set is minimized and such that the engine speed and generator electrical power output values of the operating points in the set increase or decrease monotonically.

In accordance with another aspect of the invention there is provided a computer readable signal encoded with codes for directing a processor circuit to perform a method for selecting optimal operating conditions of a genset, the genset including an engine coupled to an electrical power generator, the genset having a plurality of operating points each including an engine speed value and a generator electrical power output value, and having a plurality of cost values associated with operating the genset at respective operating points. The method involves selecting a set of operating points from the plurality of operating points such that a sum of cost values associated with operating points in the set is minimized and such that the engine speed and generator electrical power output values of the operating points in the set increase or decrease monotonically.

In accordance with another aspect of the invention there is provided a data structure for facilitating transfer of a set of operating points used in operating a genset, the genset including an engine coupled to an electrical power generator, the genset having a plurality of operating points each including an engine speed value and a generator electrical power output value, and having a plurality of cost values associated with operating the genset at respective operating points. The data structure includes a set of operating points, each operating point including an engine speed data element and a linked power output data element, the engine speed data elements in the set having values that minimize a sum of the cost values associated with operating the genset at respective operating points, the engine speed data elements and the power output data elements in the set having monotonically increasing or decreasing values.

In accordance with another aspect of the invention there is provided a method for producing a plurality of cost values associated with operating a genset at respective operating points, the genset including an engine coupled to an electrical power generator, the genset having a plurality of operating points each including an engine speed value and a generator electrical power output value. The method involves assigning weights to each of a plurality of operating conditions associated with operating the genset, the weights representing a desired trade-off between the plurality of operating conditions, receiving operating condition values corresponding to each of the plurality of operating conditions, the operating condition values associated with operating the genset at each of the plurality of operating points. The method further involves producing the cost values for each operating point by combining the operating condition values in accordance with the weights for each respective operating point.

Receiving the operating condition values may involve one of receiving a computer readable signal encoded with codes representing the operating condition values, and reading a computer readable medium encoded with codes representing the operating condition values.

Receiving may involve receiving a set of data values representing expected values of the operating conditions.

The method may involve producing a signal representing a real-time value of at least one of the operating condition values and receiving may involve receiving the signal.

Receiving the operating condition values may involve receiving values representing at least one of a fuel consumption level, a nitrogen-oxide emission level, a carbon monoxide emission level, a hydrocarbon emission level and a particulate matter emission level.

Receiving the operating condition values may involve receiving a fuel consumption level and a level of at least one engine emission.

Assigning the weights may involve receiving user input at a user interface associated with the genset and updating the weights in accordance with the user input.

Producing the cost values may involve calculating a weighted sum of the operating condition values for each of the plurality of genset operating points.

The method may involve normalizing the operating condition values and combining the operating condition values may involve combining the normalized operating condition values.

In accordance with another aspect of the invention there is provided an apparatus for producing a plurality of cost values associated with operating a genset at respective operating points, the genset including an engine coupled to an electrical power generator, the genset having a plurality of operating points each including an engine speed value and a generator electrical power output value. The apparatus includes provisions for assigning weights to each of a plurality of operating conditions associated with operating the genset, the weights representing a desired trade-off between the plurality of operating conditions, provisions for receiving operating condition values corresponding to each of the plurality of operating conditions, the operating condition values associated with operating the genset at each of the plurality of operating point, and provisions for producing the cost values for each operating point by combining the operating condition values in accordance with the weights for each respective operating point.

The provisions for receiving the operating condition values may include one of provisions for receiving a computer readable signal encoded with codes representing the operating condition values, and provisions for reading a computer readable medium encoded with codes representing the operating condition values.

The provisions for receiving may include provisions for receiving a set of data values representing expected values of the operating conditions.

The apparatus may include provisions for producing a signal representing a real-time value of at least one of the operating condition values, and the apparatus may further include provisions for receiving the signal.

The provisions for receiving the operating condition values may include provisions for receiving values representing at least one of a fuel consumption level, a nitrogen-oxide emission level, a carbon monoxide emission level, a hydrocarbon emission level, and a particulate matter emission level.

The provisions for receiving the plurality of operating condition values may include provisions for receiving a fuel consumption level and a level of at least one engine emission.

The provisions for assigning the weights may include provisions for receiving user input at a user interface associated with the genset and provisions for updating the weights in accordance with the user input.

The provisions for producing the cost values may include provisions for calculating a weighted sum of the operating condition values for each of the plurality of genset operating points.

The apparatus may include provisions for normalizing the operating condition values prior to combining the operating condition values.

In accordance with another aspect of the invention there is provided an apparatus for producing a plurality of cost values associated with operating a genset at respective operating points, the genset including an engine coupled to an electrical power generator, the genset having a plurality of operating points each including an engine speed value and a generator electrical power output value. The apparatus includes a processor circuit, operably configured to assign weights to each of a plurality of operating conditions associated with operating the genset, the weights representing a desired trade-off between the plurality of operating conditions. The processor circuit is operably configured to receive operating condition values corresponding to each of the plurality of operating conditions, the operating condition values associated with operating the genset at each of the plurality of operating points. The processor circuit is operably configured to produce the cost values for each operating point by combining the operating condition values in accordance with the weights for each respective operating point.

The processor circuit may be operably configured to receive one of a computer readable signal encoded with codes representing the operating condition values, and a computer readable medium encoded with codes representing the operating condition values.

The processor circuit may be operably configured to receive a set of data values representing expected values of the operating conditions.

The apparatus may include a sensor operably configured to produce a signal representing a real-time value of at least one of the operating condition values and the processor circuit may be operably configured to receive the signal.

The processor circuit may be operably configured to receive operating condition values representing at least one of a fuel consumption level, a nitrogen-oxide emission level, a carbon monoxide emission level, a hydrocarbon emission level, and a particulate matter emission level.

The processor circuit may be configured to receive operating condition values representing a fuel consumption level and a level of at least one engine emission.

The processor circuit may be operably configured to receive user input at a user interface associated with the genset and to update the weights in accordance with the user input.

The processor circuit may be operably configured to calculate a weighted sum of the operating conditions for each of the plurality of genset operating points.

The processor circuit may be operably configured to normalize the operating condition values prior to combining the operating condition values.

In accordance with another aspect of the invention there is provided a computer readable medium encoded with codes for directing a processor circuit to carry out a method for producing a plurality of cost values associated with operating a genset at respective operating points, the genset including an engine coupled to an electrical power generator, the genset having a plurality of operating points each including an engine speed value and a generator electrical power output value. The method involves assigning weights to each of a plurality of operating conditions associated with operating the genset, the weights representing a desired trade-off between the plurality of operating conditions, receiving operating condition values corresponding to each of the plurality of operating conditions, the operating condition values associated with operating the genset at each of the plurality of operating points and producing the cost values for each operating point by combining the operating condition values in accordance with the weights for each respective operating point.

In accordance with another aspect of the invention there is provided a computer readable signal encoded with codes for directing a processor circuit to carry out a method for producing a plurality of cost values associated with operating a genset at respective operating points, the genset including an engine coupled to an electrical power generator, the genset having a plurality of operating points each including an engine speed value and a generator electrical power output value. The method involves assigning weights to each of a plurality of operating conditions associated with operating the genset, the weights representing a desired trade-off between the plurality of operating conditions, receiving operating condition values corresponding to each of the plurality of operating conditions, the operating condition values associated with operating the genset at each of the plurality of operating points and producing the cost values for each operating point by combining the operating condition values in accordance with the weights for each respective operating point.

In accordance with another aspect of the invention there is provided a data structure for facilitating transfer of cost value data for use in operating a genset at respective operating points, the genset including an engine coupled to an electrical power generator. The data structure includes a collection of linked data elements, the data elements including a plurality of operating points each including an engine speed value and a generator electrical power output value and a cost value corresponding to each of said operating points, each cost value representing a weighted combination of a plurality of operating conditions associated with operating the genset at the operating point.

Other aspects and features of the present invention will become apparent to those ordinarily skilled in the art upon review of the following description of specific embodiments of the invention in conjunction with the accompanying figures.

BRIEF DESCRIPTION OF THE DRAWINGS

In drawings which illustrate embodiments of the invention,

FIG. 6 is a table of operating condition values used in producing the cost values in the process shown in FIG. 5;

DETAILED DESCRIPTION

Selecting Operating Points

Figure 1:
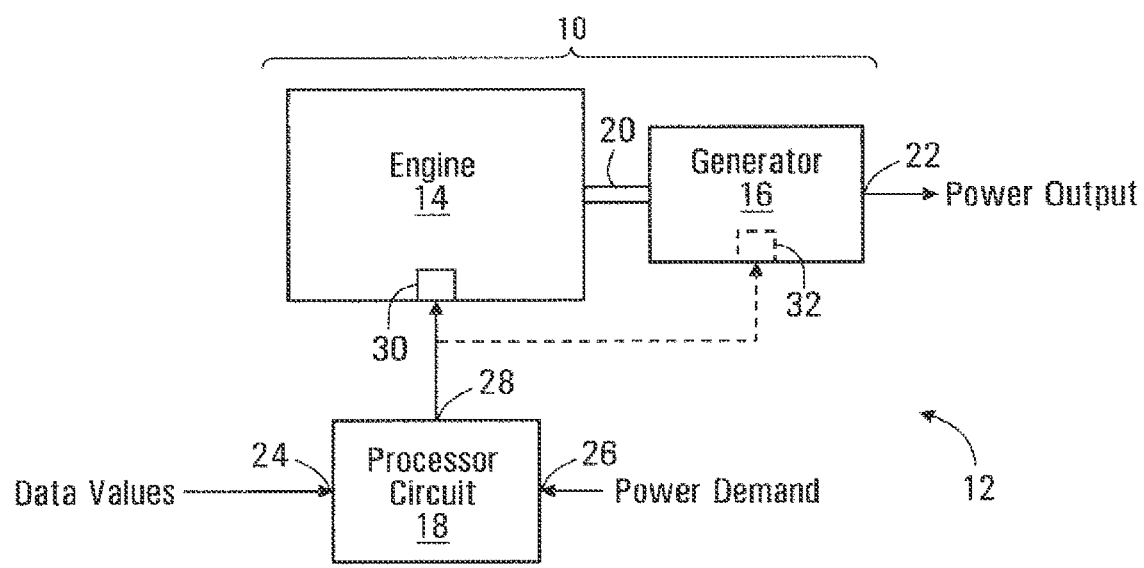
FIG. 1 is a schematic diagram of an apparatus for selecting operating conditions of a genset in accordance with a first embodiment of the invention.

Referring to FIG. 1, an apparatus for selecting operating conditions of a genset 10 is shown generally at 12. The genset 10 includes an engine 14 and a generator 16, the engine being coupled to the generator by a shaft 20. The genset 10 has a plurality of operating points, each including an engine speed value and a generator electrical power output value. The genset 10 also has a plurality of cost values associated with operating the genset at respective operating points. The apparatus 12 further includes a processor circuit 18, which is operable to select a set of operating points from the plurality of operating points such that a sum of cost values associated with operating points in the set is minimized and such that the engine speed and generator electrical power output values of the operating points in the set increase or decrease monotonically.

The generator 16 further includes an output 22 for delivering the electrical power output to be used, for example, in operation of a hybrid electric vehicle.

In the embodiment shown the processor circuit 18 also includes an output 28 for producing control signals and the engine 14 includes an interface 30 for receiving an engine control signal from the processor circuit. Optionally, the generator 16 may include an interface 32, for receiving a generator control signal from the processor circuit 18 (for example, to set a field current level in a DC electric generator).

The processor circuit 18 also includes an input 24 for receiving data values such as cost values, and an input 26 for receiving a demand to supply electrical power.

Figure 2:
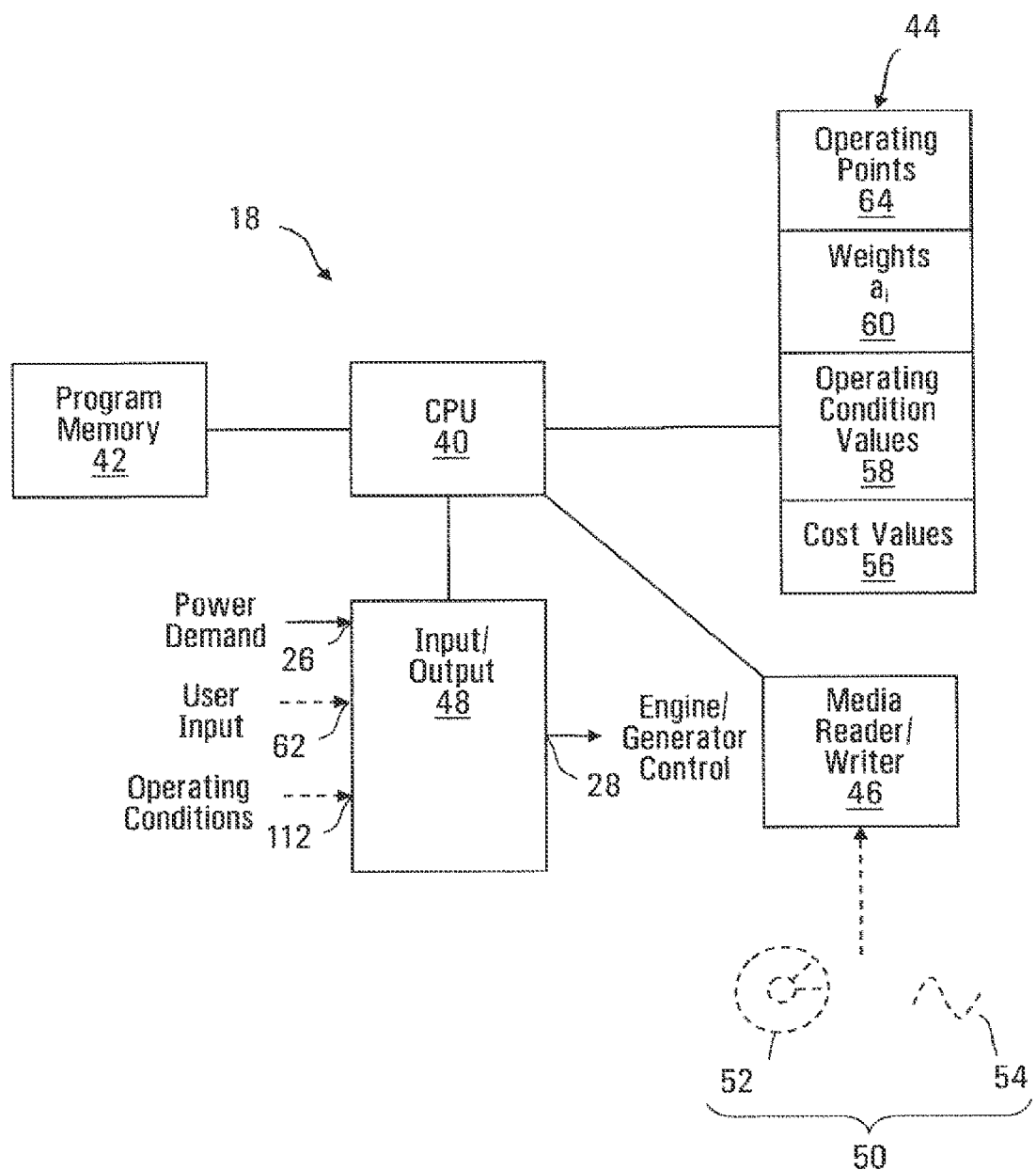
FIG. 2 is a processor circuit for use in the apparatus shown in FIG. 1.

The processor circuit 18 is shown in greater detail in FIG. 2. Referring to FIG. 2, the processor circuit 18 includes a central processing unit (CPU) 40, a program memory 42, a random access memory (RAM) 44, a media reader/writer 46, and an input output port (I/O) 48. The program memory 42, the RAM 44, the media reader/writer 46, and the I/O 48, are all in communication with the CPU 40.

The I/O 48 includes the input 26 for receiving the power demand. In the embodiment shown the I/O 48 also includes the output 28 for producing an engine/generator control signal to control the engine 14. The I/O 48 may optionally include an input 62 for receiving user input, as described later herein.

The media reader/writer 46 facilitates loading program codes into the RAM memory 44 from a computer readable medium, such as a CD ROM disk 52, or a computer readable signal 54 such as may be received from a network such as a telephone network or the internet, for example. Optionally, the plurality of cost values may be encoded on the computer readable medium 50, and the CPU 40 may be configured to load the cost values into the processor circuit 18, and store the cost values in a location 56 in the RAM 44. The RAM 44 further includes locations 58, 60, and 64 for storing operating condition values, weights $a_i$, and operating points (power output values and corresponding speed values) respectively, as described later herein.

Data Structure-Cost Values

Figure 3:
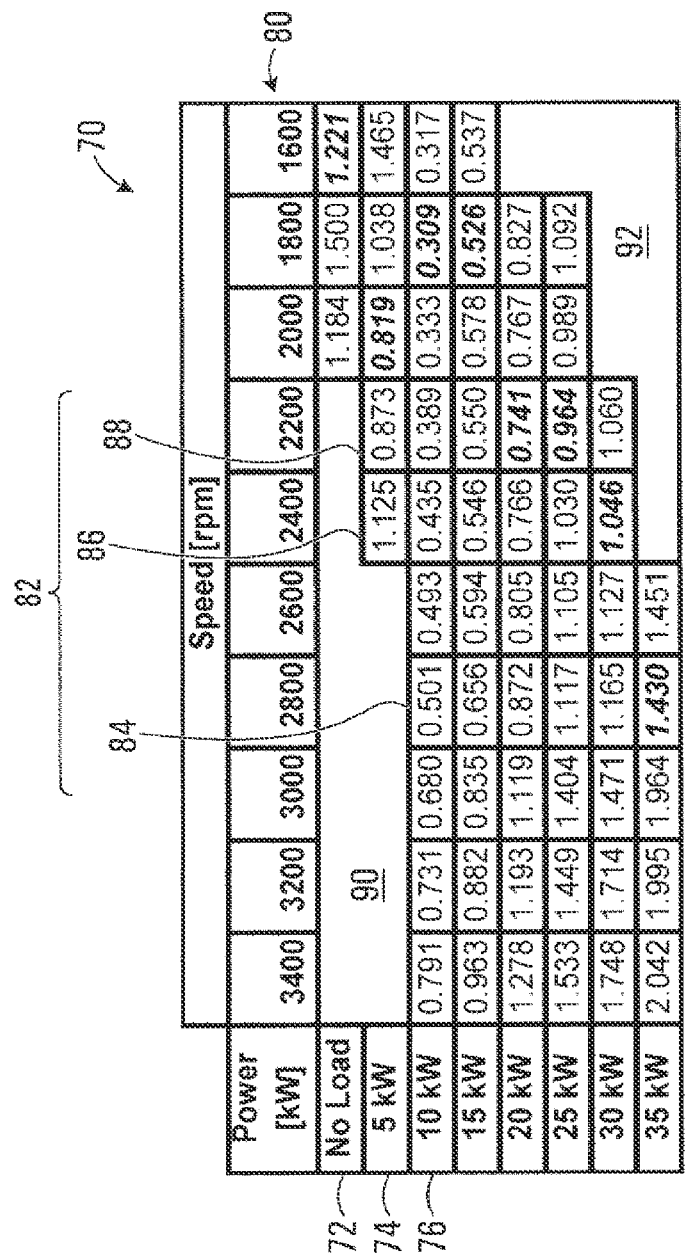
FIG. 3 is a table, depicting a data structure for use in the apparatus shown in FIGS. 1 and 2.

Referring to FIG. 3, the plurality of cost values are shown in a tabular format at 70. The table 70 includes a plurality of power output value rows 71, each row corresponding to a generator power output value that the generator is capable of supplying. In the embodiment shown in FIG. 3, the genset 10 is capable of supplying power in 5 kW increments, up to a maximum power of 35 kW. In other embodiments the power increment may be greater than or less than 5 kW, and the maximum power may be higher than 35 kW. The plurality of rows 71 includes a row 72 corresponding to a no-load power output value, a row 74 corresponding to a 5 kW power output value, a row 76 corresponding to a 10 kW power output value, etc. Each row 71 includes a plurality of rotational speeds 80 at which the genset 10 is capable of supplying power. For example, the row 76, corresponding to a 10 kW power output value, may be supplied at any of the rotational speeds 80.

Values 82, in the table 70, represent cost values associated with operating the genset 10 at various operating points, each operating point being defined by a power output value and a corresponding rotational speed 80. For example, the value 84 represents the operating cost associated with operating the genset 10 at a speed of 2800 rpm while supplying a 10 kW power output.

It may not be practical to supply some power output values at some of the listed rotational speeds 80. For example, the region 90 in the table 70 includes high rotational speeds 80 at which it may not be practical to supply low, or no load, power output values. Similarly, the region 92 in the table 70 includes low rotational speeds 80 at which it may not be practical to supply high power output values. Accordingly, in this embodiment, no cost values are assigned to operating points in the regions 90 and 92.

The plurality of values 82 in the table 70, therefore represent operating costs associated with operating at a plurality different operating points at which the genset 10 is capable of supplying electrical power.

In one embodiment data representing the table 70 is encoded on a CD-ROM disk and loaded into the location 56 in the RAM 44, shown in FIG. 2. Alternatively, the data representing the table 70 may be encoded on a computer readable signal and loaded into the location 56. The computer readable signal may be received over an internet connection, over a serial or parallel cable, a wireless connection, or any other medium for transferring data, for example.

Generating Cost Values

Figure 4:
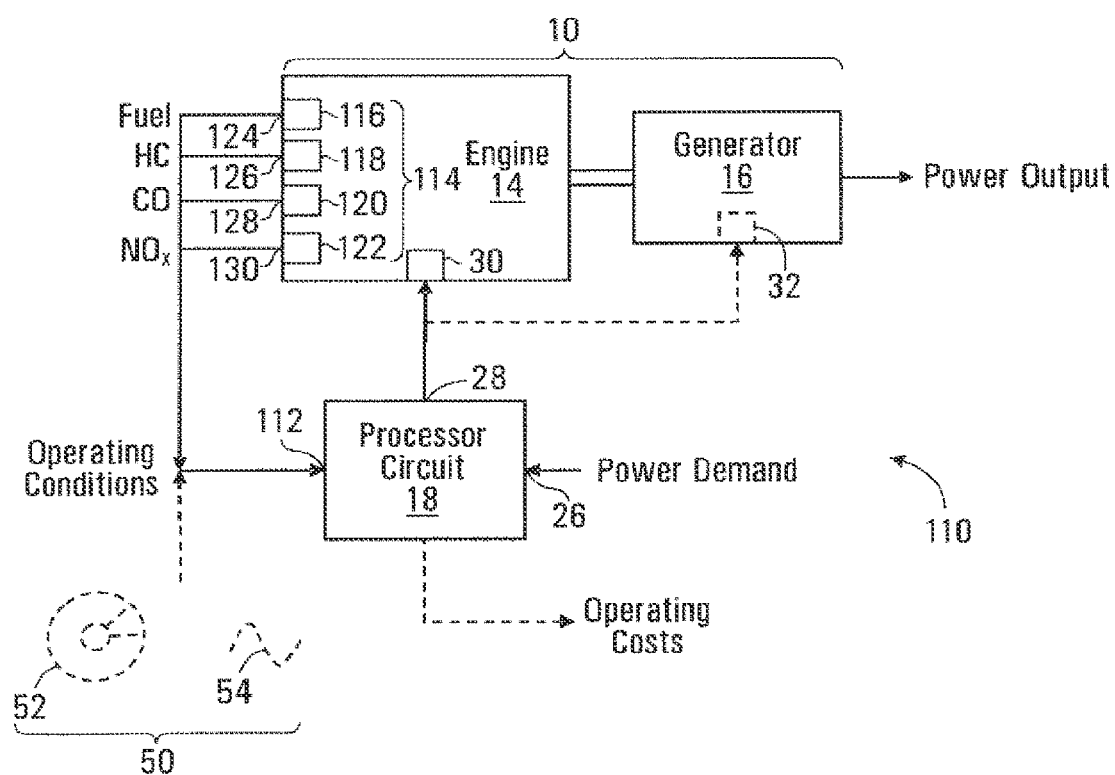
FIG. 4 is a schematic diagram of an apparatus for selecting operating conditions of a genset in accordance with a second embodiment of the invention.

Referring to FIG. 4, an apparatus for producing the plurality of cost values in accordance with one embodiment of the invention is shown generally at 110. The apparatus 110 includes the genset 10, shown in FIG. 1, and also includes the processor circuit 18, shown in FIG. 1 and FIG. 2. However, it should be understood that the apparatus 110 may be implemented using a separate processor circuit.

As described above the output 28 of the processor circuit 18 is in communication with the interface 30 of the engine 14 for controlling the engine, and optionally the output 28 may also be in communication with the interface 32 of the generator 16, for controlling the generator. The processor circuit 18 also includes an input 112 for receiving operating condition values.

The engine 14 further includes a plurality of sensors 114 for sensing operating conditions of the engine. The sensors 114 may include, for example, a fuel sensor 116, a hydrocarbon (HC) sensor 118, a carbon monoxide (CO) 120, and a nitrogen-oxide ($NO_x$) sensor 122. Other sensors may be included in the plurality of sensors 114, such as a particulate matter sensor (not shown). The sensors 114-122 each have an associated output 124-130 respectively. Each of the outputs 124-130 produces a signal representing the respective operating conditions. The outputs 124-130 are in communication with the input 112 of the processor circuit 18.

Operation—Generating Cost Values

Figure 5:
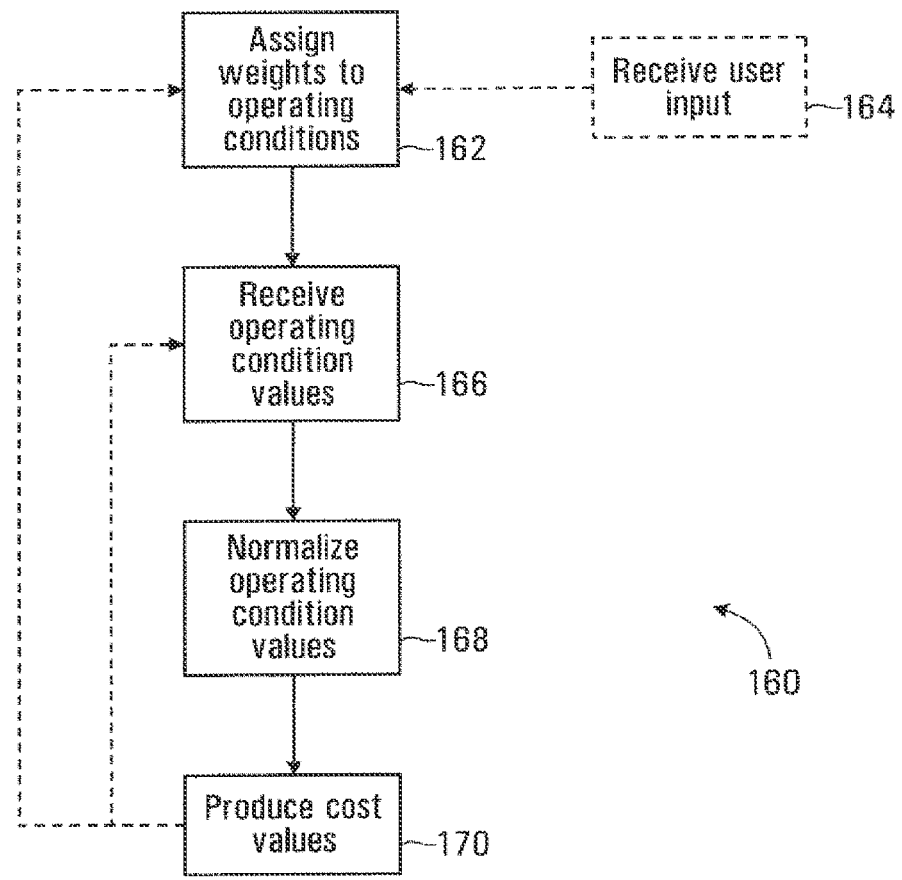
FIG. 5 is a flowchart of a process for producing cost values executed by the processor circuit shown in FIG. 2.

The operation of the apparatus 110 is described with reference to FIG. 2, FIG. 4, FIG. 5, and FIG. 6. Referring to FIG. 5, a flow chart depicting blocks of code for directing the processor circuit 18 in FIG. 2 to produce the plurality of cost values, is shown generally at 160. The blocks generally represent codes that may be read from the computer readable medium 50, and stored in the program memory 42, for directing the CPU 40 to perform various functions related to producing the plurality of cost values. The actual code to implement each block may be written in any suitable program language, such as C, C++ and/or assembly code, for example.

The process begins with a first block of codes 162, which directs the CPU 40 to assign weights $a_i$ to the operating conditions and to store the operating condition weights in the location 60 in the RAM 44.

In one embodiment the processor circuit may implement a user interface (not shown) and block 164 may optionally direct the CPU 40 to receive user input at the I/O input 62 (shown in FIG. 2). The user input may be received from a keyboard or other user input device, for example.

Block 166 directs the processor circuit 18 to receive the operating condition values from the sensors 114 (shown in FIG. 4) at the input 112. Block 166 further directs the processor circuit 18 to cause the operating condition values to be stored in the location 58 in the RAM 44.

Referring to FIG. 6 the operating condition values are presented in tabular format at 200. The table 200 includes operating condition values 224 for a plurality of operating conditions 210, including a fuel consumption operating condition 202, a hydrocarbon emission operating condition 204, a carbon monoxide emission operating condition 206, and a nitrogen oxide emission operating condition 208.

The operating condition values received from the plurality of sensors 114 may include operating condition values expressed in a number of different units of measurement. For example, the hydrocarbon, carbon monoxide, and nitrogen oxide operating condition values, which represent engine emissions, may be expressed in parts per million (ppm), while the fuel consumption operating condition value may be expressed in kilograms of fuel consumed per hour of operation (kg/h). Accordingly, block 168 directs the processor circuit 18 to normalize the operating condition values stored in the location 58 of the RAM 44.

The operating condition values 224 in the table 200 corresponding to each of the operating conditions 210 are separately normalized such that each operating condition includes values ranging from 0.000 to 1.000. For example the fuel consumption operating condition values may generally range from 0 kg/h to about 8.4 kg/h for one particular engine 14, and the values in the table 200 are normalized so that the no load, 1600 rpm fuel consumption value is 0.000 while the 35 kW, 3400 rpm consumption value is 1.000. Operating condition values for other operating conditions are similarly normalized over the operating power range of values 222 and the engine speed range of values 220. Note that the operating condition values in the Table 200 were determined by experiment and may include noise and/or experimental error and are used herein for illustrative purposes only.

Referring back to FIG. 5, the process continues at block 170, which directs the processor circuit 18 to read the RAM 44 to retrieve the normalized operating condition values from the location 58 and to read the weights $a_i$ stored in the location 60. Block 170 further directs the processor circuit 18 to apply the weights to the operating condition values 224 to produce the cost values 82 in the table 70 (shown in FIG. 3). The cost values 82 in the table 70 were generated by applying the function below to the normalized operating condition values in the table 200:

$$O_j = \sum_{i=1}^{n} a_i \cdot C_i \qquad \text{(Equation 1)}$$

where $O_j$ are the cost values associated with the plurality of operating points, $C_i$ are the operating condition values 224 corresponding to the plurality of operating conditions 210. For sake of simplicity, in generating the cost values in the table 70 the weights $a_i$ were set to unity, which assigns equal weight to each of the operating conditions 210.

Other cost value combination functions may also be used to combine the cost values $C_i$ in other ways.

The operating condition values 224 in the table 200 may be produced by operating the genset 10 (shown in FIG. 4) at the power output values 222 while receiving signals from the sensors 114, which represent the real-time values of the operating conditions 210.

In other embodiments the operating condition values may be produced before operating the genset 10. For example a manufacturer of the engine 14 may provide expected operating condition values for a specific type of engine. Alternatively the operating condition values may be established by performing tests on an engine of type and/or performance similar to the engine 14. Such values may be provided on the computer readable medium 50 and may be loaded into the processor circuit 18 using a media reader, such as the media reader/writer shown at 46 in FIG. 2.

Referring back to FIG. 5, in embodiments where at least one of the operating condition values is a real-time value provided by a sensor 114 the processor circuit may periodically repeat execution of the blocks 166, 168, and 170, thereby producing a new set of cost values based on changed operating condition values.

In other embodiments, it may desirable to alter the weights $a_i$ over time to compensate for changes in environment or the genset 10, in which case the blocks 166 to 170 may be repeated with the updated weights, thus producing new cost values 82.

Finding Local Minimum Cost Values

Referring back to FIG. 3, a minimum cost value for each power output row 71 may easily be identified by inspection of the values 82, or by performing a simple linear search for a minimum value in the row. However, in some embodiments the genset 10 may include a larger plurality of possible operating points, in which case a simple linear search for a minimum value for each power output row 71 may be slow or impractical, particularly in real-time implementations.

In one embodiment, a golden section search is used to find the minimum cost value at each successive power output value. The golden section search is a bracketing technique, which may be applied to a set of values to find a single minimum value in the set between an upper bound bracket value and a lower bound bracket value. The search begins by selecting upper and lower bound brackets at end points of the range of engine speeds 80 in the table 70. The upper and lower bound brackets are then successively narrowed until a minimum is found. The technique derives its name from the golden ratio, which has been found to be an effective bracketing ratio. Applying the golden ratio involves selecting an intermediate engine speed 80 between the upper bound bracket and the lower bound bracket that is 0.38197 from one end and 0.61803 from the other end, and then moving the bracket having a greater corresponding cost value 82, to the intermediate engine speed, which then becomes the new upper or lower bound bracket. The process is then repeated until the minimum cost value coincides with either the upper bound bracket or the lower bound bracket, in which case the lesser of the cost values corresponding to the upper and lower bound brackets is the minimum cost value.

The application of the golden section search technique to finding the minimum cost value for each power output row 71 is described with reference to the row 76 of the table 70. The first step in the application of the technique is to select 1600 rpm as the lower bound bracket and 3400 rpm as the upper bound bracket, and to calculate an intermediate point between the upper bound bracket and the lower bound bracket using the golden section ratio of 0.38197, yielding an intermediate point of 2287 rpm. The speed value 2200 rpm the closest value to the calculated intermediate value of 2287 rpm. Since the cost value at 3400 rpm is 0.791, which is larger than the cost values at 2200 rpm and 1600 rpm, a new upper bound bracket of 2200 rpm is selected. Using the new upper bound bracket of 2200 rpm and the lower bound bracket of 1600 rpm, the golden ratio is again applied to find an intermediate point, which in this case evaluates to 1829 rpm. This intermediate point is closest to the 1800 rpm speed value. Again the upper bound bracket value of 2200 rpm has a corresponding cost value of 0.550 which is larger than the cost values at 1800 and 1600 rpm. Accordingly the new upper bound bracket is chosen at 1800 rpm. Because there are no intermediate values between the 1800 rpm upper bound bracket value and the 1600 rpm lower bound bracket value, the minimum of these two values represents the minimum cost value in the row 76, which in this case is 0.526 or 1800 rpm.

Advantageously the golden section search allows quick convergence on a minimum value in a plurality of values having a single minimum between an upper bound and a lower bound. Referring to FIG. 3, the minimum cost value for each power output row 71 is indicated in bold italic typeface in the table 70.

Selecting Operating Points

A set of operating points corresponding to each of the bolded costs values in the table 70, would minimize the overall genset operating cost. However such a set of values would result in a rotational speed of the engine increasing in a somewhat sporadic manner in response to monotonically increasing power output values 71. For example, if the output power were to increase from a no load value to 15 kW, the operating speed at no load would start at 1600 rpm, and then jump to 2000 rpm as the power output is increased to 10 kW, and then the speed would reduce to 1800 rpm again at 15 kW. While such a set of operating points may optimize the sum of the cost values shown in the table 70, other operating conditions such as the lifetime of the engine, mechanical stresses in the engine, drivability for hybrid vehicle implementations, and other factors, may not be optimized by selecting these local minimum cost values at each power output value.

Accordingly an additional constraint is placed on the selection of the set of operating values. The additional constraint requires that the engine speed increase (or decrease) monotonically with monotonically increasing (or decreasing) electrical power output value. Accordingly, in response to each increase in power output value, the engine speed value should either stay the same or should increase.

In general, selecting an optimal set of operating points involves selecting a set of operating points from the table 70. This involves selecting a particular rotational speed at each power output value, and then computing a sum of the cost values for the set of operating points. A set of operating points that has the lowest sum of cost values, while meeting the constraint of monotonically increasing speed, will be the optimal set of operating points.

The sum of cost values for a set of operating points may be written as:

$$\text{Sum} = \sum_{j=1}^{n} O_j \quad \text{(Equation 2)}$$

where $O_j$ are the cost values 82 at each of n power output values 71 (in FIG. 3 n=8).

In general, when operating the genset 10, some power outputs may be more frequently used than other power outputs. For example, when operating a hybrid electric vehicle, power output values proximate a midpoint of the range of power outputs that the generator is capable of supplying, may be more frequently used than power output values at a lower end and a higher end of the range. Accordingly, in one embodiment, the sums may be computed using the function below:

$$\text{Sum} = \sum_{j=1}^{n} b_j \cdot O_j \quad \text{(Equation 3)}$$

where $b_j$ are weights that cause cost values corresponding to more frequently demanded power output values to be assigned greater weight in the sum than cost values corresponding to less frequently demanded electrical power output values. In a hybrid electric vehicle, the weights $b_j$ may be used to reflect real world drive cycles when the vehicle is operated in a particular terrain. The weight factors may further be modified when genset operating conditions change, thus facilitating adaptation of the genset to a changing environment.

Dynamic Programming Selection Technique

In one embodiment a dynamic programming technique is used to select the set of operating points for the genset 10. In dynamic programming an optimization problem is divided into sub-optimization problems, which are successively optimized to obtain an overall optimized solution. In the following description, for sake of clarity it is assumed that the weights $b_j$ are all unity (i.e. all power output values have the same importance as per Equation 2). In practice, higher weights may be set for some operating conditions that other operating conditions in accordance with the relative impact of the various conditions on the environment, and/or the cost of operating the genset, for example.

Figure 7:
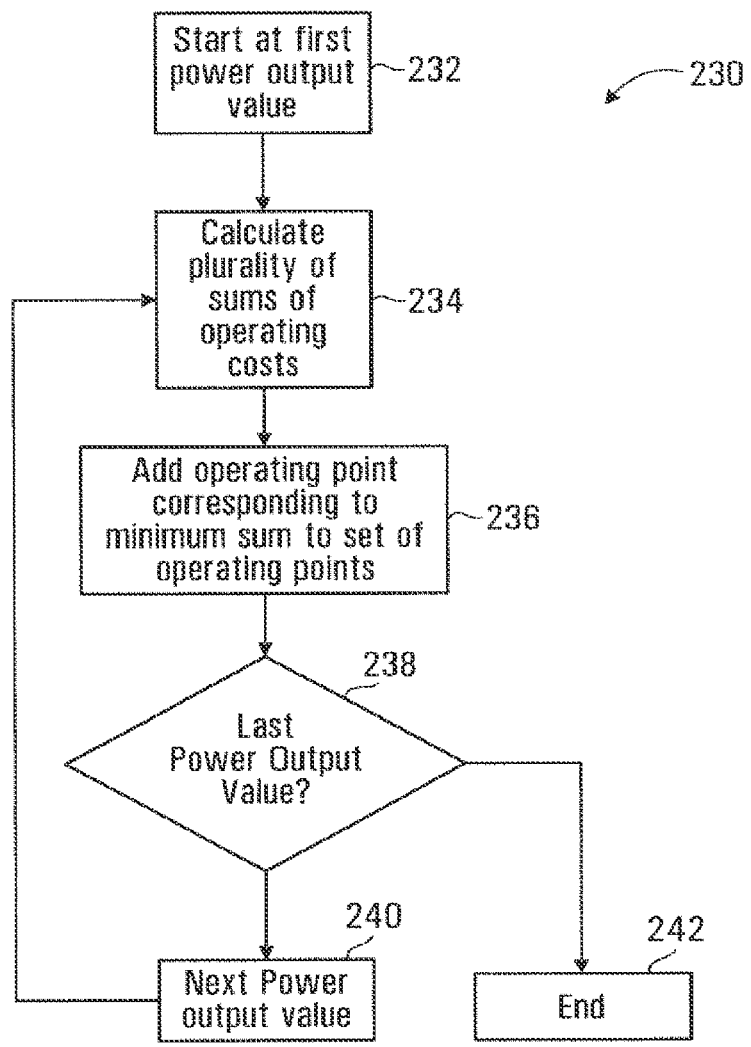
FIG. 7 is a flowchart of a process for selecting a set of operating conditions executed by the processor circuit shown in FIG. 2.

The selection of the set of operating points using a dynamic programming algorithm is described with reference to FIG. 3, FIG. 7, and FIG. 8. Referring to FIG. 7 a flow chart depicting blocks of code for directing the processor circuit 18 (shown in FIG. 2) to select the set of operating conditions, is shown generally at 230. The blocks generally represent codes that may be read from the computer readable medium 50, and stored in the program memory 42, for directing the CPU 40 to perform various functions related to producing the plurality of cost values. The actual code to implement each block may be written in any suitable program language, such as C, C++ and/or assembly code, for example.

The process begins with a first block of codes 232, which directs the processor circuit 18 to retrieve the first power output value from the location 64 of the RAM 44.

Figure 8:
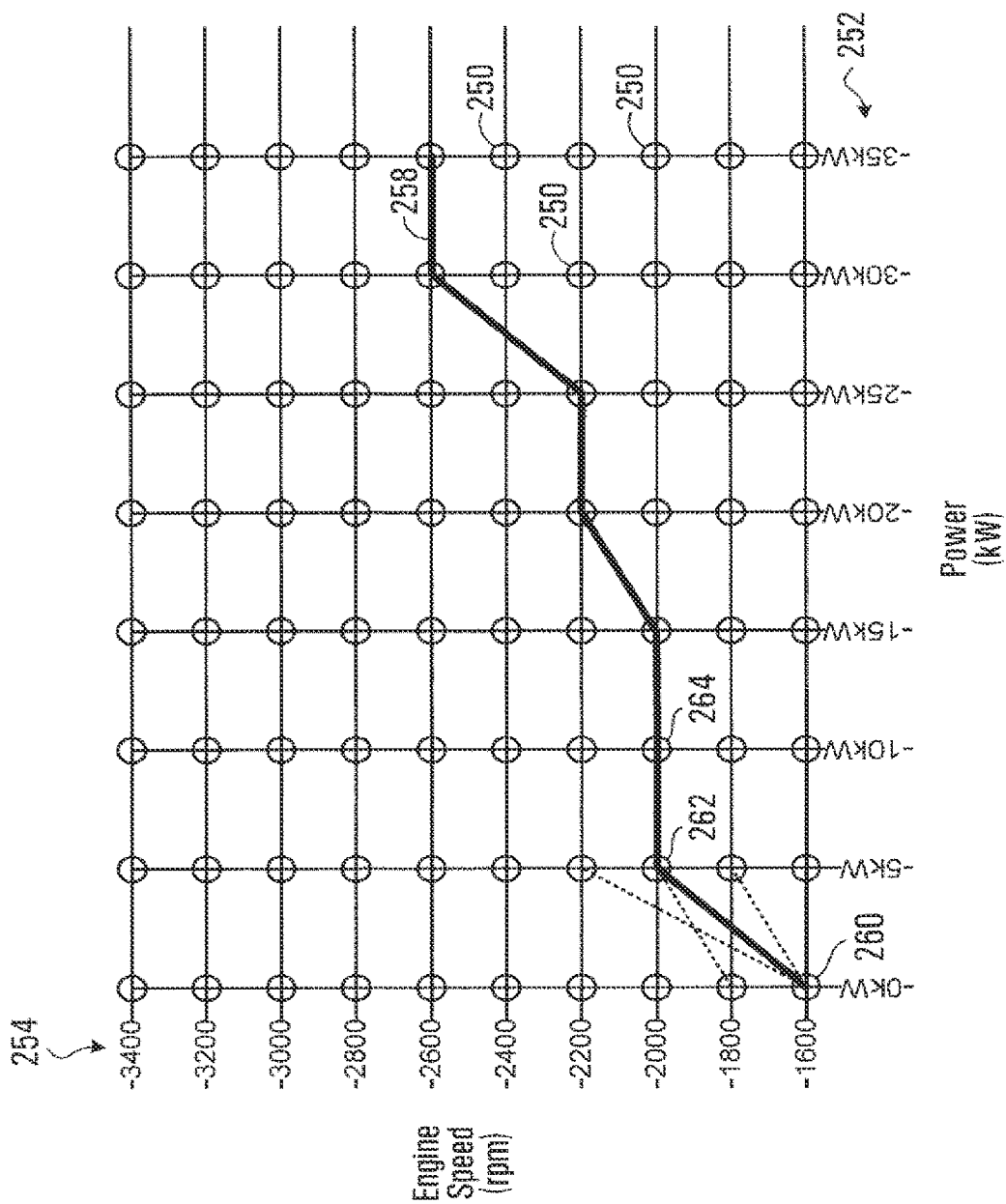
FIG. 8 is a graphical depiction of the operating points selected in the process shown in FIG. 7.

FIG. 8 shows a graphical depiction of the operating points 82 shown in FIG. 3, where each circle 250 represents an operating point having a particular power output value 252 (x-axis), and a particular rotational speed 254 (y-axis). The first power output value 252 is 0 kW. However in other embodiments the optimization may start at a maximum power output value, for example.

Referring back to FIG. 7, the process continues at block 234 which directs the processor circuit 18 to calculate the sum of cost values at the first power output value of 0 kW.

Referring to FIG. 3, at a no-load power output value (0 kW), the minimum cost for the power output value row 72 in the table 70 occurs at 1600 rpm. Block 236 thus directs the processor circuit 18 to select the engine speed 1600 rpm as the first operating point, since this point has a minimum cost value. The operating point is shown in FIG. 8 at 260. Since the minimum cost value in the row 72 is selected, the sum of cost values is the minimum operating cost at 0 kW (i.e. Sum=1.221).

Block 238 directs the processor circuit 18 to determine whether the present power output value is the last power output value. If "NO", then the process continues at block 240, where the next power output value is read from the RAM 44 at location 64. The process then returns to block 234.

The next power output value (5 kW) is read from the operating points stored in the location 64 in the RAM 44. Block 234 again directs the processor circuit to calculate the sum of cost values. At a 5 kW power output, any of the speeds 1600 rpm-3400 rpm would satisfy the constraint of monotonically increasing the speed as the power output is increased. Since the minimum cost (0.819) meets the constraint, the sum of this cost value and the cost value at 0 kW will result in minimum sum of operating costs up to and including the 5 kW power output value (i.e. Sum=1.221+ 0.819=2.040). Block 236 thus directs the processor circuit to add the operating point 262 to the set of operating points. The process continues as described above through 10 kW to 35 kW power output values.

At 10 kW power output, the speeds 2000 rpm-3400 rpm would all satisfy the constraint of monotonically increasing the speed. However, even though the minimum cost for the power output value row 76 occurs at 1800 rpm, the speed 1800 rpm (and 1600 rpm) would not satisfy the constraint. At this point in the process, an operating point 264 corresponding to a speed of 2000 rpm, which meets the constraint but is not a minimum cost operating point, may be selected.

Alternatively, one or more of the previously selected operating points in the set may be changed, such that the minimum cost value in row 76 may be selected while meeting the constraint. The decision of which alternative to select made by calculating a plurality of cost value sums corresponding to possible sets of operating points leading to the minimum cost value (0.309 @ 1800 rpm) and other cost values such as 0.317 @ 1600 rpm and 0.333 @ 2000 rpm, for example. From the plurality of cost value sums, a set of operating points that yields a minimum sum is selected. For the values of cost values indicated in the table 70, the minimum sum occurs for the operating point set (0 kw, 1600 rpm), (5 kW, 2000 rpm), (10 kW, 2000 rpm). If however, the minimum sum of cost values were to correspond to a different set of operating points, this may have resulted in changing a previously selected operating point in the set. For example, if the minimum sum had corresponded to the set of operating points (0 kw; 1600 rpm), (5 kW, 1800 rpm), (10 kW, 1800 rpm), then the operating point at 5 kW would have been changed from 2000 rpm to 1800 rpm.

If at block 238 the power output value is at the last power output value, then the process ends at block 242.

It may be appreciated that for each value in the power output value rows 71, when calculating the sums of cost values, some portions of the sums may already have been calculated at a previous power value. For example, when optimizing at 5 kW output power, at least the sum from 1600 rpm to 2000 rpm would have been calculated (Sum=221+ 0.819=2.040). Thus, when optimizing at 10 kW, in calculating the sum corresponding to the set of operating points (0 kw; 1600 rpm), (5 kW, 2000 rpm), (10 kW, 2000 rpm), the sum from 1600 rpm to 2000 rpm has already been calculated as 2.040. Accordingly, the number of calculations that are required at each power output value may be reduced by memorizing results of previous calculations. Memorization is a technique used to speed up computer programs by storing the results of previous calculations for re-use, rather than re-computing them each time. Advantageously, memorizing has a significant effect in reducing the number of operations required in selecting a set of operating points, thus facilitating computationally efficient selection of operating points for the genset 10, when faced by a changing operating condition or change in either of the weights $a_i$ or $b_j$.

Referring again to FIG. 8, the process is successively applied at each of the power output values 252 up to a 35 kW power output value until a complete set of operating points has been selected as indicated by the bold line 258.

In the above description, for simplicity it was initially assumed that the weights $b_j$ were all set to unity in accordance with Equation 2. The weights $b_j$ are simply taken into account when applying the dynamic programming technique by calculating the sums in accordance with Equation 3 using weights $b_i$ having differing values to account for real-world conditions of use of the genset.

Hybrid Electric Vehicle Application

Figure 9:
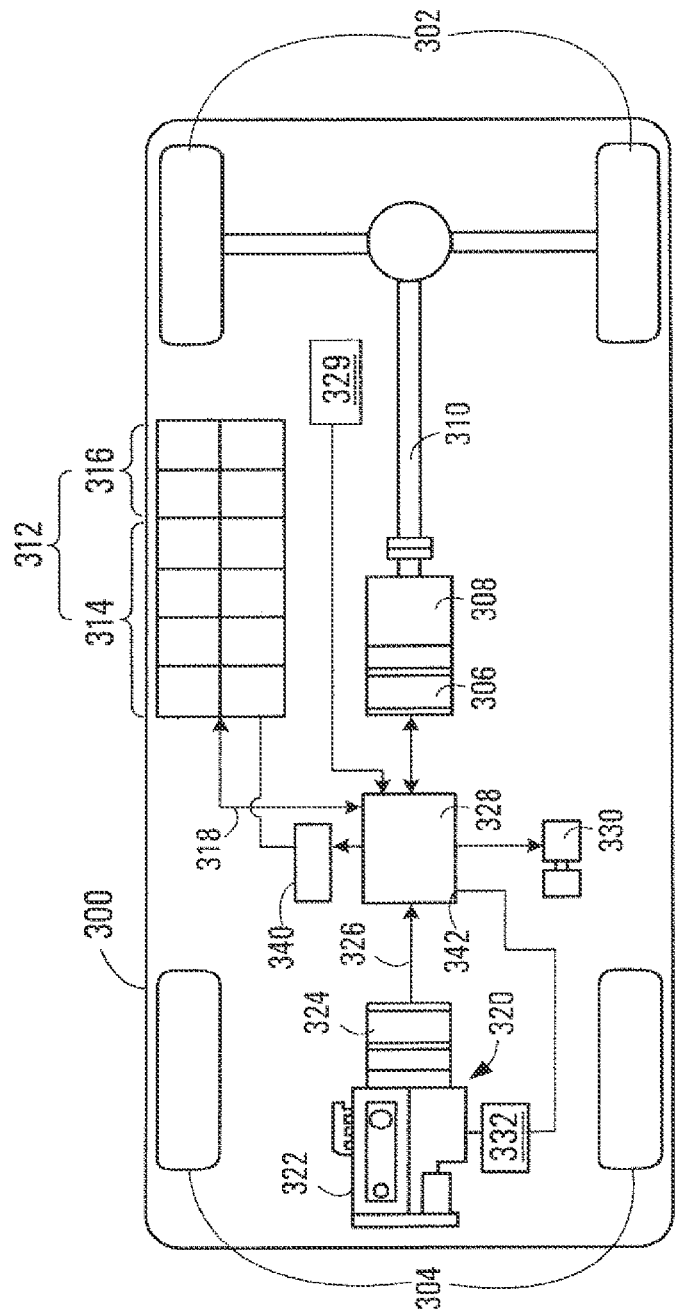
FIG. 9 is a schematic diagram of a hybrid electric vehicle.

Referring to FIG. 9, a hybrid electric vehicle embodiment of the invention is shown generally at 300. The hybrid vehicle 300 includes a first pair of driven wheels 302 and a second pair of wheels 304. The hybrid vehicle 300 further includes an electric drive motor 306, a gearbox 308 and a coupling shaft 310. The drive motor 306 is coupled to the driven wheels 302 through the gearbox 308 and the coupling shaft 310, to provide mechanical power to the driven wheels.

The hybrid vehicle 300 also includes a storage element 312, which in this embodiment includes a plurality of storage batteries 314 and a plurality of capacitor storage elements. The storage element 312 is in communication with a first energy bus 318. In one embodiment the batteries 314 are nickel metal hydride cells (NiMH), and the capacitor 316 includes one or more ultracapacitors. In other embodiments the storage element 312 may include batteries only, ultracapacitors only, or may include a flywheel energy storage element. Flywheel energy storage elements generally operate by accelerating an electrically coupled flywheel rotor in a motor/generator to a high speed thus storing inertial energy in the flywheel for later use.

The hybrid vehicle 300 further includes a genset 320, which as described above includes an engine 322 coupled to an electrical generator 324. The generator is in communication with a second energy bus 326. The genset 320 also includes a processor circuit 332, which may be the processor circuit 18 shown in FIGS. 1, 2, and 4.

The engine 320 may be any type of internal or external combustion engine, e.g. Otto, Atkinson and diesel cycle engines, Stirling engines, gas turbine engines etc. The engine 320 may also run on any type of fuel such as gasoline, diesel, biogas or other bio-fuels including cellulosic and other ethanols, propane etc.

The hybrid vehicle 300 also includes a controller 328, which is in communication with the first and second energy busses 318 and 326, for receiving electrical energy, and is also in communication with the drive motor 306 for supplying energy to the drive motor to drive the wheels 302. The controller may include various voltage converters such as a DC-DC converter for example to convert the electrical energy received on the busses 318 and 326 into a voltage suitable for supplying the drive motor 306. The controller 328 further includes an output 342 for producing power demand signals. The output 342 is in communication with the processor circuit 332.

In this embodiment the hybrid vehicle 300 includes a storage element controller 340, which is in communication with the storage element 312 for monitoring a state of charge of the storage element 312. The storage element controller 340 is also in communication with the controller 328 for providing a state of charge signal associated with a state of charge of the storage element 312 to the controller.

The hybrid vehicle also includes a foot pedal 329 for producing a signal representing a requested power to the drive motor for driving the wheels. The foot pedal 329 is in communication with the controller 328 and is disposed in a driving compartment (not shown) of the hybrid vehicle 300.

In this embodiment the hybrid vehicle also includes an accessory 330, such as compartment lighting, a wiper motor, a compartment cooling fan, etc. The controller 328 is in communication with the accessory 330 for supplying electrical energy to the accessory at a suitable voltage & current (e.g. at 12V DC).

Operation of the Hybrid Vehicle

When an operator of the hybrid vehicle 300 depresses the foot pedal 329, a signal representing a requested power associated with an amount of depression of the foot pedal is produced. The controller 328 receives the requested power signal from the foot pedal 329, and the state of charge signal from the storage element controller 340, and responds by producing a power demand signal at the output 342 for demanding a power output from the genset 320. The power output demanded from the genset 320 by the controller 328 depends on the state of charge of the storage element 312 and the power request signal received from the foot pedal 329. The power demand signal produced by the controller 328 may also include an additional demand for supplying power to the accessory 330.

The power requested by the operator's depression of the foot pedal 329 may thus be supplied by the storage element 312 over the bus 318, by the genset 320 over the bus 326, or by a combination of both. The request for drive power to be delivered to the wheels 203 is thus satisfied by power supplied by the genset 320 alone, or by the storage element 312 alone, or by a combination of a first portion of power supplied by the storage element and a second portion of power supplied by the genset.

Alternatively, if the storage element 312 is discharged, then the storage element controller produces a state of charge signal indicating that charging of the storage element 312 is required. The controller 328 then responds by producing a power demand signal to the genset 320 that includes an additional demand for power to charge the storage element 312, and the genset 320 is required to generate power for satisfying both the power request from the foot pedal 329, and a power demand for charging the storage element 312.

When the operator removes releases the foot pedal 329 without disengaging the gearbox 308, causing the hybrid vehicle 300 to coast, power from the wheels 302 drive the motor 306 thus generating electrical power, which advantageously may be coupled through the controller 328 to charge the storage element 312. If the storage element is fully charged this power may need to be dissipated in a resistor, for example.

The processor circuit 332 and genset 320 operates as described above in connection with the genset 10 and the processor circuit 18. In the embodiment shown, the processor circuit 332 receives a set of operating points (for example the operating points shown in FIG. 8 at 258) that have been determined externally to the vehicle 300 and stored on a computer readable medium, such as the computer readable medium 50 shown in FIG. 2. The set of operating points is then read into the processor circuit 332 using a media reader, such as the media reader/writer 46 shown in FIG. 2. When operating the hybrid vehicle 300, the genset 320 receives the power demand signal from the controller 328, and responds by running the engine 322 at an engine speed corresponding to the operating point in the set of operating points that corresponds to the demanded power. The generator 324 responds by supplying the demanded level of power to the energy bus 326.

Alternatively, in another embodiment, the cost values 82 (shown in FIG. 3) may be determined externally to the hybrid vehicle 300, stored on a computer readable medium, and read into the processor circuit 332 using a media reader. The processor circuit 332 may further be configured to generate a record of received demands for power outputs during operation of the genset 320 over a period of time. The processor circuit 332 then calculates the weights $b_j$, assigning greater weight to more frequently used power output values, according to the record of received demands. When the weights $b_j$ have been updated, the processor circuit 332 is configured to select the set of operating points using the externally supplied cost values, as described above. Advantageously, in this embodiment the vehicle 300 is able to adapt to a change in environment (for example, when moving the vehicle from a substantially flat terrain, to mountainous terrain) by changing the weights $b_j$.

In another embodiment, the operating condition values (shown in FIG. 6) may be read into the vehicle by a media reader into the processor circuit 332, and the cost values may be calculated on-board the hybrid vehicle 300, thereby facilitating on-board changes to the weights $a_i$ in accordance with Equation 1 for altering a desired-trade off between the various operating conditions. Advantageously, in this embodiment the vehicle 300 is able to select new operating points reflecting a different desired trade off between the operating conditions. For example, when operating the vehicle in a city environment, emissions may have to meet stricter criteria than in more rural environments, and the weights $a_i$ may be changed to reflect this difference.

In yet another embodiment, at least some of the operating condition values are provided by on-board sensors, such as the sensors 114 shown in FIG. 4. In this embodiment, the operating condition values, cost value values and the selection of a set of operating points for the genset 320 all take place in on-board the vehicle 300 in the processor circuit 332. Furthermore, in this embodiment, since the operating conditions are represented by real-time signals from the sensors 114, it may be more important to be able to quickly select a new set of operating points in response to changing operating condition values. Advantageously, the use of a dynamic programming technique provides a computationally efficient method for selecting the operating points, thus reducing a hardware speed requirement for the processor circuit 332. The sensing of operating condition values thus facilitates a quick response to changing conditions such as changes in fuel consumption patterns or emissions, due to changes in engine operation over time, for example.

The hybrid vehicle 300 shown in FIG. 9 represents an example of what is often referred to as a "serial hybrid vehicle", in that the engine 322 is not mechanically coupled to the wheels 302. Other configurations of hybrid vehicles may include engines that are coupled to both a generator and to a drive wheel of the vehicle, and may be referred to as "parallel hybrid vehicles". At least some of the above described embodiments of the invention may be applicable to various configurations of parallel hybrid vehicles, where an engine is coupled to a generator. For example, when a hybrid vehicle is at a standstill and no power is being provided to the wheels, the engine and generator may be operated using operating points selected as described above.

Other Optimization Methods

Other optimization methods may also be used to select the set of operating points for the gensets 10 or 320. In general an optimization method is a search method that is able effectively to find a condition, which minimizes the function in Equation 1 or Equation 2, subject to the constraint of monotonically increasing speed. One possible alternative is to compute every possible sum in the range of power output values and engine speeds. Such a "brute force" technique is easy to implement but has the potential downside of being slow in execution. Where quick response is required for onboard selection of operating points, more efficient techniques such as steepest descent method, conjugate gradients method, variable metric method, Newton's method, linear programming (including golden search), may be used in place of dynamic programming.

The method of steepest descent approaches the minimum in a zig-zag manner, where the new search direction is orthogonal to the previous search direction. However this method converges slowly, since after each step the method searches in an opposite direction. The method of conjugate gradients attempts to alleviate this problems with steepest descent methods to by "learning" from experience. Newton's method results in faster convergence, but not necessarily less computing time compared against steepest descent and conjugate gradient methods.

While specific embodiments of the invention have been described and illustrated, such embodiments should be considered illustrative of the invention only and not as limiting the invention as construed in accordance with the accompanying claims.

What is claimed is:

1. A method for selecting operating conditions of a genset comprising an engine coupled to an electrical power generator, the genset having a plurality of operating points each comprising an engine speed value and a generator electrical power output value, the method comprising:
   determining a plurality of cost values corresponding to respective ones of the operating points,
   selecting a set of operating points from the plurality of operating points such that:
      a sum of the cost values corresponding to the operating points in the selected set is minimized; and
      the engine speed values of the operating points in the selected set increase or decrease as a function of the generator electrical power output values of the operating points in the selected set;
      wherein the sum of the cost values corresponding to the operating points in the selected set is determined by assigning a weight to one or more of the operating points in the selected set, and wherein greater weights are assigned to operating points having electrical output values proximate a midpoint of a range of power outputs that the electrical power generator is capable of supplying.

2. The method of claim 1, wherein greater weights are assigned to operating points having more frequently demanded electrical power outputs values.

3. The method of claim 1, wherein assigning said weight comprises assigning greater weight to electrical power output values proximate a midpoint of a range of power outputs that the generator is capable of supplying.

4. The method of claim 1, further comprising generating a record of received demands for power outputs during operation of the genset over a period of time, and wherein assigning said weights comprises assigning greater weight to more frequently used power output values.

5. The method of claim 4, wherein generating said record comprises generating said record and updating said weights while operating the genset and wherein selecting further comprises selecting a new set of operating points when said weights have been updated.

6. The method of claim 1, wherein selecting comprises:
   successively applying a dynamic programming algorithm to select sets of operating points at successive power output values within a range of power outputs the generator is capable of supplying; and
   selecting a set of operating points corresponding to a last power output value in said range as said set of operating points for said genset.

7. The method of claim 6 wherein, applying said dynamic programming algorithm comprises:
   producing a first plurality of sums of cost values at a first power output value;
   memorizing a result of at least one of said first plurality of said sums; and
   using at least some of said memorized results for producing a further sum of cost values at a subsequent power output value.

8. The method of claim 7, wherein selecting comprises locating a minimum cost value at each power output value and wherein successively applying said dynamic programming algorithm comprises first producing said sums of cost values corresponding to said minimum cost value at each successive power output value.

9. An apparatus for selecting operating conditions of a genset comprising an engine coupled to an electrical power generator, the genset having a plurality of operating points each comprising an engine speed value and a generator electrical power output value, the apparatus comprising:
   a processor circuit configured to determine a plurality of cost values corresponding to respective ones of the operating points, and to select a set of operating points from the plurality of operating points such that:
      a sum of the cost values corresponding to the operating points in the selected set is minimized; and
      the engine speed values of the operating points in the selected set increase or decrease as a function of the generator electrical power output values of the operating points in the selected set;
   wherein the sum of the cost values corresponding to the operating points in the selected set is determined by assigning a weight to one or more of the operating points in the selected set, wherein greater weights are assigned to operating points having electrical output values proximate a midpoint of a range of power outputs that the electrical power generator is capable of supplying.

10. The apparatus of claim 9, wherein the processor circuit is configured to assign greater weights to operating points having more frequently demanded electrical power outputs values.

11. The apparatus of claim 9, wherein the processor circuit is configured to assign greater weight to electrical power output values proximate a midpoint of a range of power outputs that the generator is capable of supplying.

12. The apparatus of claim 9, wherein the processor circuit is configured to generate a record of received demands for power outputs during operation of the genset over a period of time and to assign greater weight to more frequently used power output values.

13. The apparatus of claim 12, wherein the processor circuit is configured to generate said record and update said weights while operating the genset and to select a new set of operating points when said weights have been updated.

14. The apparatus of claim 9, wherein the processor circuit is configured to:
   successively apply a dynamic programming algorithm to select sets of operating points at successive power output values within a range of power outputs the generator is capable of supplying; and
   select a set of operating points corresponding to a last power output value in said range as said set of operating points for said genset.

15. The apparatus of claim 14 wherein the processor circuit is configured to:
   produce a first plurality of sums of cost values at a first power output value;
   memorize a result of at least one of said first plurality of said sums; and
   use at least some of said memorized results for producing a further sum of cost values at a subsequent power output value.

16. The apparatus of claim 15, wherein the processor circuit is configured to locate a minimum cost value at each power output value and to apply said dynamic programming to first produce said sums of cost values corresponding to said minimum cost value at each successive power output value.

17. A hybrid vehicle comprising a genset including an engine coupled to an electrical power generator, the genset having a plurality of operating points each comprising an engine speed value and a generator electrical power output value, the hybrid vehicle comprising:
   a processor circuit configured to determine a plurality of cost values corresponding to respective ones of the operating points, and to select a set of operating points from the plurality of operating points such that:
      a sum of the cost values corresponding to the operating points in the selected set is minimized; and
      the engine speed values of the operating points in the selected set increase or decrease as a function of the generator electrical power output values of the operating points in the selected set;
   wherein the sum of the cost values corresponding to the operating points in the selected set is determined by assigning a weight to one or more of the operating points in the selected set, wherein greater weights are assigned to operating points having electrical output values proximate a midpoint of a range of power outputs that the electrical power generator is capable of supplying.

18. The hybrid vehicle of claim 17, wherein the processor circuit is configured to assign greater weights to operating points having more frequently demanded electrical power outputs values.

19. The hybrid vehicle of claim 17, wherein the processor circuit is configured to assign greater weight to electrical power output values proximate a midpoint of a range of power outputs that the generator is capable of supplying.

20. The hybrid vehicle of claim 17, wherein the processor circuit is configured to generate a record of received demands for power outputs during operation of the genset over a period of time and to assign greater weight to more frequently used power output values.

21. The hybrid vehicle of claim 20, wherein the processor circuit is configured to generate said record and update said weights while operating the genset and to select a new set of operating points when said weights have been updated.

22. The hybrid vehicle of claim 17, wherein the processor circuit is configured to:

successively apply a dynamic programming algorithm to select sets of operating points at successive power output values within a range of power outputs the generator is capable of supplying; and select a set of operating points corresponding to a last power output value in said range as said set of operating points for said genset.

23. The hybrid vehicle of claim 22 wherein the processor circuit is configured to:

produce a first plurality of sums of cost values at a first power output value;

memorize a result of at least one of said first plurality of said sums; and use at least some of said memorized results for producing a further sum of cost values at a subsequent power output value.

24. The hybrid vehicle of claim 23, wherein the processor circuit is configured to locate a minimum cost value at each power output value and to apply said dynamic programming to first produce said sums of cost values corresponding to said minimum cost value at each successive power output value.

\* \* \* \* \*